United States Patent
Kangas et al.

(10) Patent No.: US 10,244,988 B2
(45) Date of Patent: Apr. 2, 2019

(54) METHOD, APPARATUS AND COMPUTER PROGRAM OF USING A BIO-SIGNAL PROFILE

(75) Inventors: Jari Kangas, Tampere (FI); Leo Kärkkäinen, Helsinki (FI); Mikko Nurmi, Tampere (FI); Ville Ojanen, Espoo (FI); Ilka Salminen, Tampere (FI); Sunil Sivadas, Tampere (FI); Akos Vetek, Helsinki (FI)

(73) Assignee: NOKIA TECHNOLOGIES OY, Espoo (FI)

( * ) Notice: Subject to any disclaimer, the term of this patent is extended or adjusted under 35 U.S.C. 154(b) by 233 days.

(21) Appl. No.: 12/970,595

(22) Filed: Dec. 16, 2010

(65) Prior Publication Data

US 2012/0157789 A1    Jun. 21, 2012

(51) Int. Cl.
A61B 5/00    (2006.01)
G06F 3/01    (2006.01)

(52) U.S. Cl.
CPC .......... *A61B 5/7228* (2013.01); *A61B 5/7285* (2013.01); *A61B 5/7296* (2013.01); *G06F 3/011* (2013.01); *G06F 3/015* (2013.01); *A61B 5/7246* (2013.01); *A61B 5/742* (2013.01); *A61B 5/7405* (2013.01)

(58) Field of Classification Search
CPC .............................. G06F 3/015; G07F 17/3206
See application file for complete search history.

(56) References Cited

U.S. PATENT DOCUMENTS

| | | | | |
|---|---|---|---|---|
| 4,003,379 A | * | 1/1977 | Ellinwood, Jr. | A61B 5/0468 128/DIG. 1 |
| 5,360,971 A | * | 11/1994 | Kaufman et al. | 250/221 |
| 5,539,860 A | * | 7/1996 | DeSimone et al. | 704/234 |
| 7,502,643 B2 | | 3/2009 | Farringdon et al. | |
| 2002/0069211 A1 | * | 6/2002 | Kondo | A61B 5/00 |
| 2003/0060728 A1 | * | 3/2003 | Mandigo | G11B 19/02 600/545 |
| 2003/0176806 A1 | * | 9/2003 | Pineda et al. | 600/544 |
| 2003/0179229 A1 | * | 9/2003 | Van Erlach et al. | 345/744 |
| 2003/0181795 A1 | * | 9/2003 | Suzuki et al. | 600/300 |

(Continued)

FOREIGN PATENT DOCUMENTS

| | | |
|---|---|---|
| EP | 1 830 292 A1 | 9/2007 |
| EP | 1 975 783 A1 | 10/2008 |

(Continued)

OTHER PUBLICATIONS

PCT International Search Report and Written Opinion for PCT/IB2011/055713; dated May 9, 2012; 12 pages; ISA/SE.

(Continued)

*Primary Examiner* — Gary Jackson
*Assistant Examiner* — Zahed Kabir
(74) *Attorney, Agent, or Firm* — Alston & Bird LLP

(57) ABSTRACT

A method, apparatus and computer program wherein the method includes: obtaining, from a detector, a detection of at least one bio-signal of a user of an apparatus; determining a mode of operation of the apparatus when the at least one bio-signal occurred; and correlating the at least one detected bio-signal of the user with the determined mode of operation in a bio-signal profile of the user of the apparatus.

17 Claims, 3 Drawing Sheets

(56) References Cited

U.S. PATENT DOCUMENTS

Figure 1:
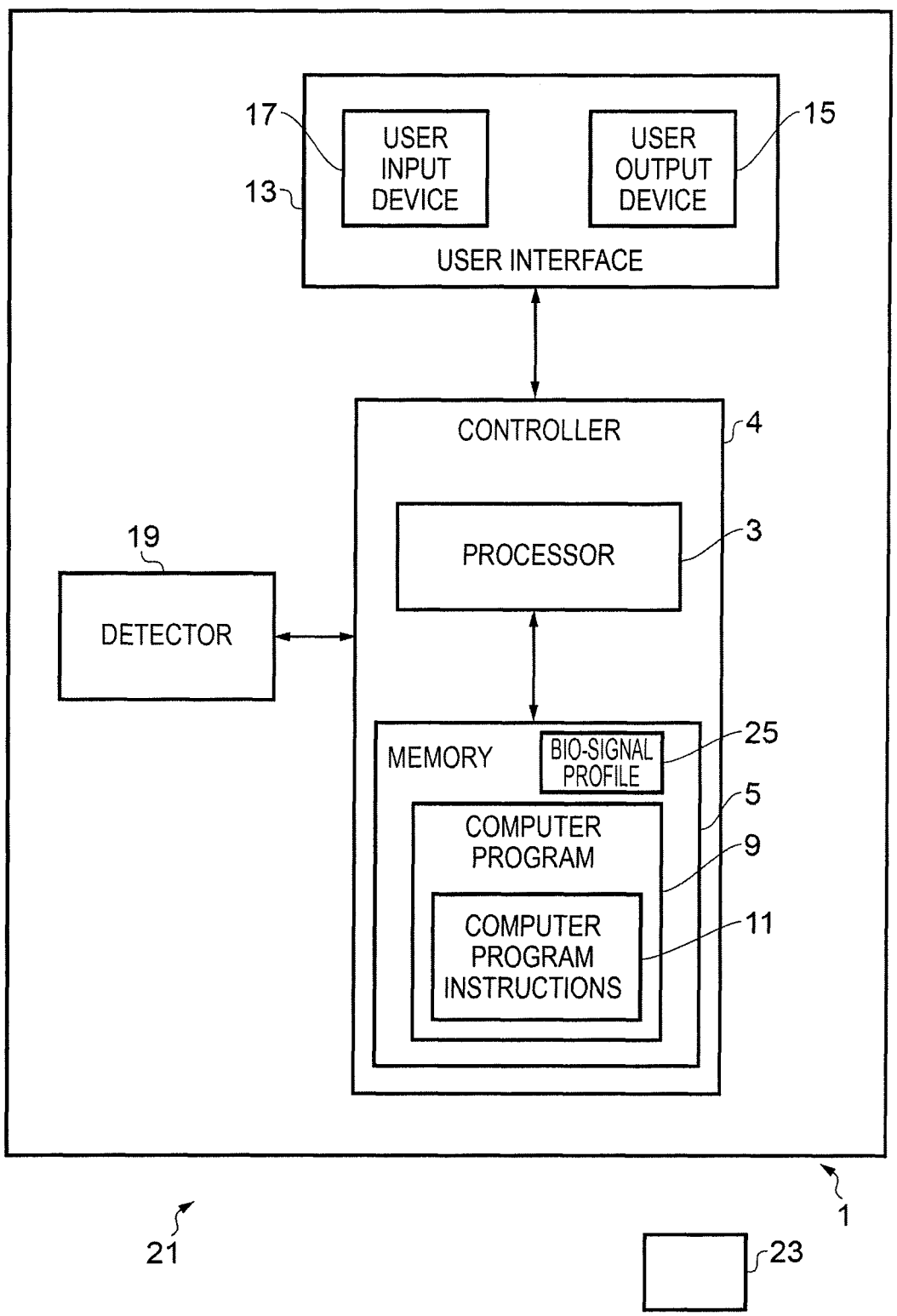

| | | | |
|---|---|---|---|
| 2005/0124463 A1* | 6/2005 | Yeo | A61B 5/02427 482/8 |
| 2006/0143647 A1* | 6/2006 | Bill | 725/10 |
| 2006/0224046 A1* | 10/2006 | Ramadas et al. | 600/300 |
| 2007/0060831 A1* | 3/2007 | Le | A61B 5/0476 600/544 |
| 2008/0208015 A1* | 8/2008 | Morris et al. | 600/301 |
| 2009/0055132 A1 | 2/2009 | Cheng et al. | |
| 2009/0105785 A1* | 4/2009 | Wei | A61N 1/36132 607/48 |
| 2009/0149718 A1* | 6/2009 | Kim | A61B 5/0006 600/300 |
| 2009/0195497 A1* | 8/2009 | Fitzgerald et al. | 345/156 |
| 2010/0011388 A1* | 1/2010 | Bull et al. | 725/9 |
| 2010/0022279 A1* | 1/2010 | Hoberg et al. | 455/567 |
| 2010/0090835 A1 | 4/2010 | Liu et al. | |
| 2010/0094097 A1* | 4/2010 | Liu et al. | 600/300 |
| 2011/0071364 A1* | 3/2011 | Kuo | A61B 5/0002 600/300 |
| 2011/0179054 A1* | 7/2011 | Westerink et al. | 707/758 |
| 2011/0260830 A1* | 10/2011 | Weising | G06F 3/015 340/5.52 |
| 2012/0016208 A1* | 1/2012 | Janssen | G06F 17/30764 600/300 |
| 2012/0086630 A1* | 4/2012 | Zhu | A63F 13/355 345/156 |

FOREIGN PATENT DOCUMENTS

| | | |
|---|---|---|
| EP | 2 179 770 A1 | 4/2010 |
| WO | WO 03/073175 A2 | 9/2003 |
| WO | WO 2006/043925 A1 | 4/2006 |
| WO | WO 2009/109903 A1 | 9/2009 |

OTHER PUBLICATIONS

Extended European Search Report from corresponding European Patent Application No. 11848553.1 dated May 31, 2016.
Office Action for Vietnamese Application No. 1-2013-01967 dated May 7, 2018, 3 pages.
Office Action for Chinese Application No. 2011800655898 dated Sep. 5, 2018.

\* cited by examiner

METHOD, APPARATUS AND COMPUTER PROGRAM OF USING A BIO-SIGNAL PROFILE

TECHNOLOGICAL FIELD

Embodiments of the present invention relate to a method apparatus and computer program. In particular, they relate to a method, apparatus and computer program for providing a personalized output to a user.

BACKGROUND

Many apparatus provide a plurality of different outputs to a user. For example an apparatus may be used both for communications functions and for entertainment functions such as enabling a user to play games or listen to music.

It may be useful to enable the functions of the apparatus to be personalized for the user. This may make the apparatus easier and more convenient for the user to use.

BRIEF SUMMARY

According to various, but not necessarily all, embodiments of the invention there is provided a method comprising: obtaining, from a detector, a detection of at least one bio-signal of a user of an apparatus; determining a mode of operation of the apparatus when the at least one bio-signal occurred; and correlating the at least one detected bio-signal of the user with the determined mode of operation in a bio-signal profile of the user of the apparatus.

In some embodiments of the invention the bio-signal profile may comprise data collected over a period of time relating to a plurality of different modes of operation of the apparatus and correlated bio-signals.

In some embodiments of the invention the bio-signal profile may be unique to the user of the apparatus.

In some embodiments of the invention the bio-signal profile may provide an indication of a range of normal bio-signals of the user when the apparatus is in a given mode of operation. The method may further comprise obtaining, from the detector, a detection of a further bio-signal and determining the mode of operation of the apparatus when the further bio-signal occurred and comparing the further bio-signal and mode of operation with the bio-signal profile to determine whether or not the further bio-signal is within the normal range.

In some embodiments of the invention the method may also comprise enabling an output of the apparatus to be modified if the further bio-signal is outside the normal range. The output which is modified may comprise a user interface.

In some embodiments of the invention the at least one bio-signal may comprise a signal which originates from a human being.

In some embodiments of the invention the correlating the at least one detected bio-signal of the user with the determined mode of operation may comprise associating the at least one detected bio-signal of the user with the determined mode of operation so that they may be stored together.

According to various, but not necessarily all, embodiments of the invention there is provided an apparatus comprising: at least one processor; and at least one memory including computer program code; wherein the at least one memory and the computer program code are configured to, with the at least one processor, enable the apparatus to: obtain, from a detector, a detection of at least one bio-signal of a user of an apparatus; determine a mode of operation of the apparatus when the at least one bio-signal occurred; and correlate the at least one detected bio-signal of the user with the determined mode of operation in a bio-signal profile of the user of the apparatus.

In some embodiments of the invention the bio-signal profile may comprise data collected over a period of time relating to a plurality of different modes of operation of the apparatus and correlated bio-signals.

In some embodiments of the invention the bio-signal profile may be unique to the user of the apparatus.

In some embodiments of the invention the bio-signal profile may provide an indication of a range of normal bio-signals of the user when the apparatus is in a given mode of operation.

In some embodiments of the invention the at least one memory and the computer program code may be configured to, with the at least one processor, further enable the apparatus to obtain, from the detector, a detection of a further bio-signal and determine the mode of operation of the apparatus when the further bio-signal occurred and compare the further bio-signal and mode of operation with the bio-signal profile to determine whether or not the further bio-signal is within the normal range.

In some embodiments of the invention the at least one memory and the computer program code may be configured to, with the at least one processor, enable the apparatus to modify an output of the apparatus if the further bio-signal is outside the normal range.

In some embodiments of the invention the output which is modified may comprise a user interface.

In some embodiments of the invention the at least one bio-signal may comprise a signal which originates from a human being.

In some embodiments of the invention the correlating the at least one detected bio-signal of the user with the determined mode of operation may comprise associating the at least one detected bio-signal of the user with the determined mode of operation so that they may be stored together.

According to various, but not necessarily all, embodiments of the invention there is provided a computer program comprising computer program instructions that, when executed by at least one processor, enable an apparatus at least to perform: obtaining, from a detector, a detection of at least one bio-signal of a user of an apparatus; determining a mode of operation of the apparatus when the at least one bio-signal occurred; and correlating the at least one detected bio-signal of the user with the determined mode of operation in a bio-signal profile of the user of the apparatus.

In some embodiments of the invention there may be provided a computer program comprising program instructions for causing a computer to perform the method as described in any of the preceding paragraphs.

In some embodiments of the invention there may be provided a physical entity embodying the computer program as described in any of the preceding paragraphs.

In some embodiments of the invention there may be provided an electromagnetic carrier signal carrying the computer program as described in any of the preceding paragraphs.

According to various, but not necessarily all, embodiments of the invention there is provided a method comprising: determining a mode of operation of an apparatus; obtaining, from a detector, a detection of at least one bio-signal of a user of the apparatus; comparing the at least one obtained bio signal and the determined mode of operation with a bio-signal profile; and providing an output of the apparatus in dependence upon the comparison with the bio-signal profile.

In some embodiments of the invention the bio-signal profile may provide an indication of a range of normal bio-signals of the user when the apparatus is in the determined mode of operation.

In some embodiments of the invention a first output may be provided if the user is determined to be in a first context and a second, different output may be provided if the user is determined to be in a second context.

In some embodiments of the invention a first context of the user may be that the user is providing bio-signals within the range of normal bio-signals and a second context of the user may be that the user is providing bio-signals outside the range of normal bio-signals.

In some embodiments of the invention the output which is provided may comprise a user interface.

According to various, but not necessarily all, embodiments of the invention there is provided an apparatus comprising: at least one processor; and at least one memory including computer program code; wherein the at least one memory and the computer program code are configured to, with the at least one processor, enable the apparatus to: determine a mode of operation of an apparatus; obtain, from a detector, a detection of at least one bio-signal of a user of the apparatus; compare the at least one obtained bio signal and the determined mode of operation with a bio-signal profile; and provide an output of the apparatus in dependence upon the comparison with the bio-signal profile.

In some embodiments of the invention the bio-signal profile may provide an indication of a range of normal bio-signals of the user when the apparatus is in a given mode of operation.

In some embodiments of the invention a first output may be provided if the user is determined to be in a first context and a second, different output may be provided if the user is determined to be in a second context.

In some embodiments of the invention a first context of the user may be that the user is providing bio-signals within the range of normal bio-signals and a second context of the user may be that the user is providing bio-signals outside the range of normal bio-signals.

In some embodiments of the invention the output which is provided may comprise a user interface.

According to various, but not necessarily all, embodiments of the invention there is provided a computer program comprising computer program instructions that, when executed by at least one processor, enable an apparatus at least to perform: determining a mode of operation of an apparatus; obtaining, from a detector, a detection of at least one bio-signal of a user of the apparatus; comparing the at least one obtained bio-signal and the determined mode of operation with a bio-signal profile; and providing an output of the apparatus in dependence upon the comparison with the bio-signal profile.

In some embodiments of the invention there may be provided a computer program comprising program instructions for causing a computer to perform the method as described in any of the preceding paragraphs.

In some embodiments of the invention there may be provided a physical entity embodying the computer program as described in any of the preceding paragraphs.

In some embodiments of the invention there may be provided an electromagnetic carrier signal carrying the computer program as described in any of the preceding paragraphs.

The apparatus may be for wireless communication.

BRIEF DESCRIPTION

Figure 2:
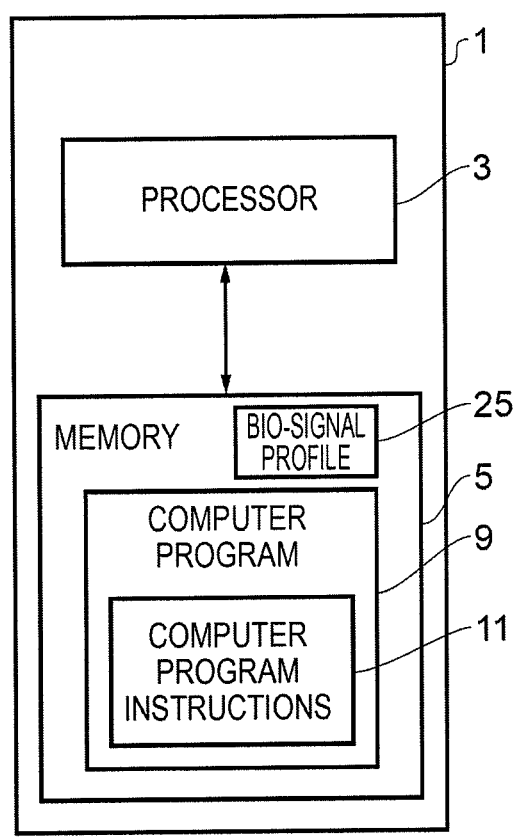
Figure 3:
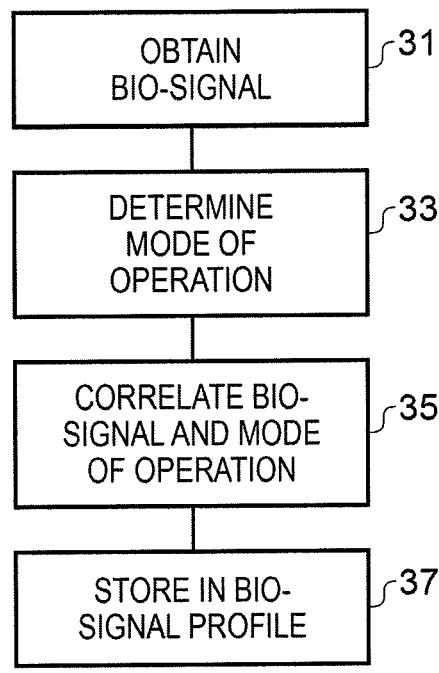
Figure 4:
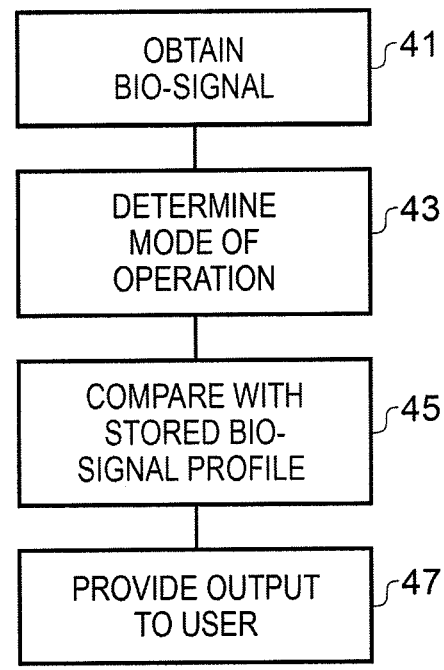

For a better understanding of various examples of embodiments of the present invention reference will now be made by way of example only to the accompanying drawings in which:

FIG. 1 schematically illustrates an apparatus according to an exemplary embodiment of the invention;

FIG. 2 schematically illustrates an apparatus according to another exemplary embodiment of the invention;

FIG. 3 is a block diagram which schematically illustrates a method according to an exemplary embodiment of the invention; and FIG. 4 is a block diagram which schematically illustrates a method according to another exemplary embodiment of the invention.

DETAILED DESCRIPTION

Embodiments of the invention relate to collecting data relating to the emotional or physiological state of a user when they are using an apparatus 1. The data may be collected by obtaining bio-signals from a detector 19 and storing information relating to the obtained bio-signal. The data relating to the emotional or physiological state of the user may be stored along with an indication of the functions being performed by the apparatus 1 when the data was collected. This data could then be used to create a profile of the user of the apparatus 1 which could then be used to personalize the functions of the apparatus 1.

The Figures illustrate a method comprising: obtaining 31, from a detector 19, a detection of at least one bio-signal of a user of an apparatus 1; determining 33 a mode of operation of the apparatus 1 when the at least one bio-signal occurred; and correlating 35 the at least one detected bio-signal of the user with the determined mode of operation in a bio-signal profile 25 of the user of the apparatus 1.

The Figures also illustrate a method comprising: determining 41 a mode of operation of an apparatus 1; obtaining 43, from a detector 19, a detection of at least one bio-signal of a user of the apparatus 1; comparing 45 the at least one obtained bio signal and the determined mode of operation with a bio-signal profile 25; and providing 47 an output of the apparatus 1 in dependence upon the comparison with the bio-signal profile 25.

FIG. 1 schematically illustrates an apparatus 1 according to embodiments of the invention. The apparatus 1 may be an electronic apparatus. The apparatus 1 may be, for example, a mobile cellular telephone, a personal computer, a camera, a gaming device, a personal digital assistant, a personal music player, a tablet computer, a mounted head display a wearable computer, a sensing device placed under a user's skin or any other apparatus 1. The apparatus 1 may be a handheld apparatus 1 which can be carried in a user's hand, handbag or jacket pocket for example.

Only features referred to in the following description are illustrated in FIG. 1. However, it should be understood that the apparatus 1 may comprise additional features that are not illustrated. For example in some embodiments of the invention the apparatus may comprise means for transmitting and receiving communication signals which enable the apparatus to communicate within one or more communication networks such as a cellular network.

The apparatus 1 illustrated in FIG. 1 comprises: a user interface 13, a detector 19 and a controller 4. In the illustrated embodiment the controller 4 comprises at least one processor 3 and at least one memory 5 and the user interface 13 comprises a user output device 15 and a user input device 17. In the embodiment illustrated in FIG. 1 the detector 19 may be part of the apparatus 1. It is to be appreciated that in other embodiments of the invention the detector 19 may be remote from the apparatus 1. Also there may be a plurality of detectors 19 provided. The detectors 19 may detect different bio-signals. The data collected by the detectors 19 may be stored in a central unit. The central unit may comprise a controller 4 as illustrated in FIG. 1. In some embodiments of the invention the data may be stored in a server, the server may be a remote server or a cloud server or any other suitable location.

The controller 4 provides means for controlling the apparatus 1. The controller 4 may be implemented using instructions that enable hardware functionality, for example, by using executable computer program instructions 11 in one or more general-purpose or special-purpose processors 3 that may be stored on a computer readable storage medium 23 (e.g. disk, memory etc) to be executed by such processors 3.

The controller 4 may be configured to control the apparatus 1 to perform a plurality of different functions. For example, where the apparatus 1 is a mobile cellular telephone the controller 4 may be configured to control the apparatus 1 to make and receive telephone calls and also to perform other functions such as send messages or access communication networks such as local area networks or the internet.

The controller 4 may also be configured to enable the apparatus 1 to obtain, from a detector 19, a detection of at least one bio-signal of a user of an apparatus 1; determine a mode of operation of the apparatus 1 when the at least one bio-signal occurred; and correlate the at least one detected bio-signal of the user with the determined mode of operation in a bio-signal profile 25 of the user of the apparatus 1.

In some embodiments of the invention the controller 4 may also be configured to enable the apparatus 1 to obtain, from a detector 19, a detection of at least one bio-signal of a user of an apparatus 1; determine a mode of operation of the apparatus 1; compare the at least one detected bio-signal of the user and the determined mode of operation with a bio-signal profile 25; and provide an output the apparatus 1 in dependence upon the comparison with the bio-signal profile 25.

The at least one processor 3 is configured to receive input commands from the user interface 13 and also to provide output commands to the user interface 13. The at least one processor 3 is also configured to write to and read from the at least one memory 5. Some of the output signals of the user interface 13 may be provided as inputs to the controller 4.

The user interface 13 may comprise any means which enables the user of the apparatus 1 to interact with the apparatus 1. As illustrated schematically in FIG. 1 the user interface 13 comprises a user input device 17 and a user output device 15.

The user input device 17 may also comprise means which enables a user of the apparatus 1 to input information which may be used to control the apparatus 1. The user input device 17 may also comprise means which enable a user to input information which may be stored in the one or more memories 5 of the apparatus 1. For example the user input device 17 may comprise a keypad, a touch sensitive display, a directional input device such as a joystick or tracker or a combination of a number of different types of user input devices.

The user output device 15 may comprise any means which enables an output to be provided by the apparatus 1 to a user. In some embodiments of the invention the output which is provided may comprise a visual output such as text and/or images. In such embodiments of the invention the output device 15 may comprise a display 15 which is configured to display the text and/or images.

The display 15 may also be configured to display a graphical user interface. The graphical user interface may enable the user of the apparatus 1 to control the apparatus 1. The graphical user interface may comprise one or more selectable items which a user of the apparatus 1 may select using the user input device 17.

In some embodiments of the invention the output which is provided may comprise an audio output. In such embodiments of the invention the output device 15 may comprise a loudspeaker or any other means configured to provide an audio output.

In some embodiments of the invention a plurality of different outputs may be provided simultaneously. For example an audio output may be provided simultaneously to a visual output, for example as part of video footage or an audio alert may accompany a visual alert.

Other types of output may also be provided, for example, tactile outputs such as vibrations of the apparatus 1 may be provided as an alert or as part of gaming mode of operation.

The apparatus 1 illustrated in FIG. 1 also comprises a detector 19. The detector 19 may comprise any means which is configured to detect one or more bio-signals and provide an indication of the detected bio-signal to the controller 4.

In embodiments of the invention a bio-signal may comprise any type of signal which originates from a biological being such as a human being. A bio-signal may, for example, comprise a bio-electrical signal, a bio-mechanical signal, an aural signal, a chemical signal or an optical signal.

The bio-signal may comprise a consciously controlled signal. For example it may comprise an intentional action by the user such as the user moving a part of their body such as their arm or their eyes. In some embodiments of the invention the bio-signal may comprise a sub-consciously controlled signal. For example it may comprise a signal which is an automatic physiological response by the biological being. The automatic physiological response may occur without a direct intentional action by the user and may comprise, for example, an increase in heart rate or a brain signal. In some embodiments of the invention both consciously controlled and sub-consciously controlled signals may be detected by the detector 19.

A bio-electrical signal may comprise an electrical current produced by one or more electrical potential differences across a part of the body of the user such as tissue, organ or cell system such as the nervous system. Bio-electrical signals may include signals that are detectable, for example, using electroencephalography, magnetoencephalography, galvanic skin response techniques, electrocardiography and electromyography or any other suitable technique.

A bio-mechanical signal may comprise the user of the apparatus 1 moving a part of their body. The movement of the part of the body may be a conscious movement or a sub-conscious movement. Bio-mechanical signals may include signals that are detectable using one or more accelerometers or mechanomyography or any other suitable technique.

An aural signal may comprise a sound wave. The aural signal may be audible to a user. Aural signals may include signals that are detectable using a microphone or any other suitable means for detecting a sound wave.

A chemical signal may comprise chemicals which are being output by the user of the apparatus 1 or a change in the chemical composition of a part of the body of the user of the apparatus 1. Chemical signals may, for instance, include signals that are detectable using an oxygenation detector or a pH detector or any other suitable means.

An optical signal may comprise any signal which is visible. Optical signals may, for example, include signals detectable using a camera or any other means suitable for detecting optical signals.

In the illustrated embodiment the detector 19 is part of the apparatus 1. In other embodiments of the invention the detector 19 could be separate to the apparatus 1 but could be configured to provide an indication of a detected bio-signal to the apparatus 1 via a communication link. The communication link could be a wireless communication link. In other embodiments of the invention the communication link could be a wired communication link.

Also in the illustrated embodiment only one detector 19 is illustrated. It is to be appreciated that in embodiments of the invention a plurality of detectors 19 may be provided. The plurality of detectors 19 may be configured to detect different types of bio-signals so that a range of different bio-signals may be obtained. For example, one or more detector 19 could be configured to detect bio-electrical signals while one or more other detectors could be configured to detect bio-mechanical signals.

The at least one memory 5 stores a computer program code 9 comprising computer program instructions 11 that control the operation of the apparatus 1 when loaded into the at least one processor 3. The computer program instructions 11 provide the logic and routines that enable the apparatus 1 to perform the methods illustrated in FIGS. 3 and 4. The at least one processor 3 by reading the at least one memory 5 is able to load and execute the computer program 9.

The at least one memory 5 may also store a bio-signal profile 25. The bio-signal profile 25 may cross reference different modes of operation of the apparatus 1 with collected bio-signal data. The collected bio-signal data comprises data which has been collected while the user uses the apparatus 1. The data may be collected over an extended period of time. For example the data may be collected over a period of weeks or months. The bio-signal data may be collected every time the user of the apparatus accessed particular functions of the apparatus 1.

The collected bio-signal data may be analyzed to provide an indication of a normal range for a given bio-signal for a given mode of operation of the apparatus 1. For example all bio-signal data which is cross referenced to a given mode of operation could be analyzed to determine a threshold value for that bio-signal when the apparatus is in the given mode of operation. The threshold value could be an average value such as a mean or median value. In other embodiments of the invention the threshold value could provide an indication of an upper or lower limit. An indication of the threshold values may also be stored in the bio-signal profile 25.

Different modes of operation of the apparatus 1 will be cross referenced to different bio-signal data and so may have different threshold values of the bio-signals associated with them.

The bio-signal profile 25 may be unique to the user of the apparatus 1 because it is created from data generated by the user as they use the apparatus 1.

The computer program instructions 11 may provide computer readable program means configured to control the apparatus 1. The program instructions 11 may provide, when loaded into the controller 4; means for obtaining, from a detector, a detection of at least one bio-signal of a user of an apparatus; means for determining a mode of operation of the apparatus when the at least one bio-signal occurred; and means for correlating the at least one detected bio-signal of the user with the determined mode of operation in a bio-signal profile of the user of the apparatus.

The program instructions 11 may also provide, when loaded into the controller 4; means for determining a mode of operation of an apparatus 1; means for obtaining, from a detector, a detection of at least one bio-signal of a user of the apparatus 1; means for comparing the at least one obtained bio signal and the determined mode of operation with a bio-signal profile 25; and means for providing an output of the apparatus 1 in dependence upon the comparison with the bio-signal profile 25.

The computer program code 9 may arrive at the apparatus 1 via any suitable delivery mechanism 21. The delivery mechanism 21 may be, for example, a tangible, non-transitory, computer-readable storage medium, a computer program product 23, a memory device, a record medium such as a CD (compact disc) or DVD (digital versatile disc) or Blu-ray disc, an article of manufacture that tangibly embodies the computer program code 9. The delivery mechanism may be a signal configured to reliably transfer the computer program code 9. The apparatus 1 may propagate or transmit the computer program code 9 as a computer data signal.

Although the memory 5 is illustrated as a single component it may be implemented as one or more separate components some or all of which may be integrated/removable and/or may provide permanent/semi-permanent/dynamic/cached storage.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (e.g. Von Neumann)/parallel architectures but also specialized circuits such as field-programmable gate arrays (FPGA), application integration specific circuits (ASIC), signal processing devices and other devices. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

FIG. 2 illustrates an apparatus 1' according to another embodiment of the invention. The apparatus 1' illustrated in FIG. 2 may be a chip or a chip-set. The apparatus 1' comprises at least one processor 3 and at least one memory 5 as described above in relation to FIG. 1.

Methods of controlling an apparatus 1 to enable the transfer of data from a source apparatus to a target apparatus according to exemplary embodiments of the invention are illustrated schematically in FIGS. 3 and 4.

FIG. 3 illustrates a method of creating or updating a bio-signal profile 25 according to an exemplary embodiment of the invention. At block 31 at least one bio-signal is obtained by the controller 4. The bio-signal may be detected by the detector 19 and provided to the controller 4. In some embodiments of the invention more than one bio-signal may be obtained. As mentioned above plurality of different types of bio-signals may be obtained. This may enable a more accurate determination of the physiological and emotional state of the user to be made.

The bio-signal may comprise one or more of the different types of bio-signal as described above.

At block 33 the mode of operation of the apparatus 1 at the time the bio-signal was generated is determined. In some embodiments of the invention block 33 and block 31 may occur simultaneously. In other embodiments of the invention blocks 31 and 33 may occur sequentially but may be separated by a short period of time. The period of time may be of the order of several seconds. In such embodiments of the invention the mode of operation would be the current mode of operation of the apparatus 1.

The mode of operation may be determined by the applications which are running on the apparatus 1 or the functions being performed by the apparatus 1 when the bio-signal is generated. The different modes of operation of the apparatus 1 may include, for example, a gaming mode, a communications mode, a content rendering mode, a passive mode or any other available mode of operation.

A gaming mode of operation may enable a user of the apparatus 1 to participate in games. In some embodiments of the invention their may be a plurality of different gaming modes. A plurality of different gaming modes may be available and each different gaming mode may be associated with different games or different types of games. For example a first type of gaming mode may be associated with combative games. When a user is playing these types of games they might be expected to be in a first type of physiological or emotional state. For example, they may be in an alert state, they might show relatively high levels of stress or excitement and they might also make vigorous movements of their body in order to play the game. Another type of gaming mode could be associated with puzzles such as word or logic problems. When a user is playing these types of games they might be in a different type of physiological or emotional state. For example, they may be in a focused state in which they are concentrating hard but in which they are making very few movements of their body.

A communications mode of operation may enable the user of the apparatus 1 to communicate with other users or other apparatus 1. The communications mode may enable, for example, a user of the apparatus 1 to make and/or receive telephone calls. The communications mode may also enable a user to send and/or receive messages. The messages could be for example, SMS (short message service) or MMS (multi media service) messages, email messages or instant messages. The communication modes of operation may also enable the apparatus 1 to access a network such as the internet and download and/or upload information from the network.

A content rendering mode may enable a user to access and render content. The content may comprise audio and/or visual content. For example the content may comprise music and/or video footage. The content may be stored in the one or more memories 5 or may be stored received by the apparatus 1.

In some embodiments of the invention the apparatus 1 may have a passive mode of operation. In the passive mode of operation the apparatus 1 might not be being used by the user for any specific function however the apparatus 1 may still be configured to receive messages. In such passive states the user input device may be temporarily disabled to enable the apparatus 1 to be carried in a user's pocket or bag without inadvertently making inputs using the user input device 17.

In some embodiments of the invention the mode of operation may be determined by determining whether or not the user is focused on the apparatus 1. Bio-signals may be used to determine whether or not the user is focused on the apparatus 1, for example, the position of the user's eyes or face may be detected to determine whether or not the user is looking at the apparatus.

At block 35 the obtained bio-signal and the determined mode of operation of the apparatus 1 are correlated. The correlation of the mode of operation and the obtained bio-signal may comprise associating the mode of operation with the bio-signal so that they may be cross referenced within a bio-signal profile.

At block 37 the data indicative of the obtained bio-signal and the determined mode of operation of the apparatus 1 are stored in a bio-signal profile 25 of the user of the apparatus 1. The bio-signal profile 25 may be stored in the at least one memory 5 as described above.

The bio-signal profile 25 may comprise a plurality of different bio-signals which have been collected over a period of time each of which have been associated with the appropriate mode of operation of the apparatus 1. The plurality of different bio-signals may be analyzed to give an indication of the bio-signals which would be expected when the user is using the apparatus 1 and so provide an indication of a normal range of bio-signals for any given mode of operation.

The bio-signal information which is stored in the bio-signal profile 25 may comprise data which has been collected, over an extended period of time, while the user uses the apparatus 1. The data may be collected by using the method illustrated in FIG. 3. In some embodiments of the invention the method illustrated in FIG. 3 may be repeated at regular or predetermined intervals. In other embodiments of the invention the method may be repeated every time a particular mode of operation is enabled. This may enable more information to be included in the bio-signal profile and may make the normal range of bio-signals associated with the user more accurate.

FIG. 4 illustrates a method of using a bio-signal profile according to embodiments of the invention. The bio-signal profile may have been created using the method illustrated in FIG. 3. The method may have been repeated a plurality of times for a plurality of different modes of operation.

At block 41 a further bio-signal is obtained by controller 4 and at block 43 the current mode of operation of the apparatus 1 is determined. The further bio-signal may be detected by the detector 19 and provided to the controller 4 as described above in relation to block 31 and the current mode of operation of the apparatus 1 may be determined as described above in relation to block 33.

At block 45 the further bio-signal and mode of operation of the apparatus 1 are compared with the stored bio-signal profile 25. This comparison may enable a context of the user of the apparatus 1 to be determined. The context of the user may be the emotional or physiological state of the user of the apparatus 1 in combination with the current mode of operation of the apparatus 1. In some embodiments of the invention the context may comprise the situation of the user, for example it may be possible to determine if the user is alone or if they are accompanied by other people in a social or business situation.

In some embodiments of the invention a first context could be that the bio-signal obtained at block 41 falls within the normal range of bio-signals according to the bio-signal profile and a second context could be that the bio-signal obtained at block 41 falls outside the normal range of bio-signals. In order to determine whether or not the bio-signal obtained at block 41 falls within the normal range of bio-signals the value of the bio-signal obtained at block 41 may be compared with a threshold value of a bio-signal which may be stored in the bio-signal profile 25.

If the threshold value is an average value then the bio-signal obtained at block 41 may be considered to be within a normal range if it has less than a predetermined deviation from the threshold value. If the threshold value is an upper or lower limit then the bio-signal obtained at block 41 may be considered to be within a normal range if it is less than or higher than the upper and lower limits respectively.

In some embodiments of the invention each mode of operation of the apparatus 1 is associated with different threshold values of the bio-signals. For example higher stress levels may be expected if a user is in a combative gaming mode than if they are listening to music or having a telephone conversation.

At block 47 the controller 4 controls the apparatus 1 to provide an output to a user. The output which is provided may depend upon the comparison of the obtained bio-signal and the stored bio-signal profile 25. If the obtained bio-signal is determined to be within a normal range then a first output may be provided. If the obtained bio-signal is determined to be outside a normal range then a second, different output may be provided.

The output which is provided may also depend upon the mode of operation of the apparatus and the bio-signals which have been obtained.

For example, if a user is using the apparatus 1 to access content or create content and the obtained bio-signal indicates that the stress level of a user is normal with respect to the current mode of operation of the apparatus 1 then the graphical user interfaces and audio outputs provided to a user may be standard graphical user interfaces and audio outputs. Conversely if the obtained bio-signal indicates that the stress level of a user is higher than normal with respect to the current mode of operation of the apparatus then it may be considered that the increase in stress could be due to difficulties which the user has in using the apparatus. In order to reduce the stress levels and make the apparatus 1 easier for the user to use the graphical user interfaces and audio outputs provided to a user may be modified to provide extra assistance to the user of the apparatus 1.

In other exemplary situations it may be determined that the stress level of the user is higher than the normal stress level but that modifying the output provided to the user would not reduce the stress level because of the mode of operation of the apparatus 1. For example, if the mode of operation of the apparatus 1 is a communications mode and the apparatus 1 is being used to make a telephone call then it may be determined that the high level of stress of the user is as a consequence of the telephone call rather than an output which is controlled by the controller. Therefore it may be considered that there is no need to modify the output provided by the apparatus as this is not contributing to the stress level of the user. In such cases even though the bio-signals are outside the normal range there would be no reason to change the outputs provided the apparatus.

In another embodiment of the invention the apparatus may be in a gaming mode of operation, for example the user may be using the apparatus to play a combative game. If the obtained bio-signal were to correspond to a higher level of stress in such circumstances then it may be determined that this is merely part of the game and so the output provided by the apparatus would not be modified to help reduce the stress level.

In other embodiments of the invention whether or not the output of the apparatus) is modified may depend upon whether or not the user is focused on the apparatus 1. If it is determined that the user is focused on the apparatus 1, for example if they are looking at a display, then an output of the apparatus 1 may be modified in response to the determination of the context of the user. Conversely, if it is determined that the user is not focused on the apparatus 1, for example if they are not looking at a display, then the outputs of the apparatus 1 might not be modified as this would be less effective because the user is not focused on the apparatus 1.

Embodiments of the invention as described enable different outputs to be provided by an apparatus 1 for different emotional and physiological states of the user of the apparatus 1. By correlating the bio-signals with the current mode of operation of the apparatus 1 the embodiments of the invention take into account the fact that different bio-signals might be considered to be normal for different modes of operation of the apparatus 1. This may ensure that the most appropriate outputs are provided to take into account both the status of the user and the mode of operation of the apparatus 1.

By collecting data over a period of time and storing it in a bio-signal profile 25 the outputs provided are personal to the user of the apparatus and may be optimized to make the apparatus as convenient as possible for the user. Also by correlating the bio-signal data with the data relating to the use of the apparatus 1 this enables the bio-signal profile to be more specific and may reduce the margin of error in what is considered to be a normal range of bio-signals. This may enable the apparatus 1 to be more sensitive to changes in the emotional or physiological state of the user.

The blocks illustrated in the FIGS. 3 and 4 may represent steps in a method and/or sections of code in the computer program 9. The illustration of a particular order to the blocks does not necessarily imply that there is a required or preferred order for the blocks and the order and arrangement of the block may be varied. Furthermore, it may be possible for some blocks to be omitted.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. A method comprising:
repeatedly and automatically, obtaining a detection of at least one bio-signal of a user of an apparatus;
determining, by the apparatus, a particular mode of operation of the apparatus in which the apparatus operated when a particular changed bio-signal was detected as changing from a first state to a second state, wherein the apparatus has a plurality of different modes of operation and wherein each different mode of operation is defined by which of at least a first application or a second application is running; and using a bio-signal profile to determine an output to be provided by comparing each of the first state and the second state of the particular changed bio-signal to a normal range for the particular mode of operation according to the bio-signal profile, wherein the output is determined dependent upon (1) the particular changed bio-signal having changed (a) from being outside the normal range to inside the normal range, or (b) from being inside the normal range to outside the normal range, and (2) the particular mode of operation of the apparatus in which the apparatus operated when the particular changed bio-signal was detected as changing, wherein, in an instance in which it is determined that the particular mode of operation is a first mode of operation in which the apparatus runs the first application but not the second application, the output determined changes in response to the particular changed bio-signal changing from the first state to the second state, and wherein, in an instance in which it is determined that the particular mode of operation is a second mode of operation in which the apparatus runs the second application but not the first application, the output determined does not change in response to the particular changed bio-signal changing from the first state to the second state.

2. The method as claimed in claim 1 wherein the bio-signal profile comprises data collected for the user over a period of time relating to a plurality of different modes of operation of the apparatus and correlated bio-signals for the user, wherein respective normal ranges for modes of operation of the apparatus is provided by the bio-signal profile, wherein a first normal range of bio-signals for the first mode of operation is different to a second normal range of bio-signals for the second mode of operation.

3. The method as claimed in claim 1 further comprising: enabling an output of the apparatus to be modified if the particular changed bio-signal is outside the normal range for the particular mode of operation of the apparatus.

4. The method as claimed in claim 3 wherein the output which is modified comprises a user interface.

5. The method as claimed in claim 1, additionally comprising, repeatedly, over a time period of at least weeks, correlating, by the apparatus, the at least one detected bio-signal of the user with respective determined mode of operations and storing correlations in the bio-signal profile.

6. The method as claimed in claim 1, wherein the particular mode of operation is determined by determining whether or not the user is looking at the apparatus.

7. A method as claimed in claim 1, wherein the first state of the particular changed bio-signal is indicative of a normal emotional or physiological state of the user, and the second state of the particular changed bio-signal is indicative of a non-normal emotional or physiological state of the user, and wherein the output provided changes to prevent the emotional or physiological state of the user diverging further from the normal emotional or physiological state of the user.

8. A method as claimed in claim 1, wherein the first state of the particular changed bio-signal is indicative of a normal lower stress level and the second state of the particular changed bio-signal is indicative of a higher stress level, wherein the output changes from a first user interface to a second user interface that is predetermined as an easier-to-use user interface.

9. A method as claimed in claim 1, wherein the first state of the particular changed bio-signal is indicative of normality for the first mode of operation, the second state of the particular changed bio-signal is not indicative of normality for the first mode of operation and the first state and the second state of the particular changed bio-signal are indicative of normality for the second mode of operation.

10. A method as claimed in claim 1, wherein the first state and the second state are separated by a threshold value determined by data collected from the user at least over weeks or months.

11. A method as claimed in claim 1, wherein the at least one bio-signal comprise output from at least one of an accelerometer, or aural signal, or position of the user's eyes or face or facial expressions.

12. A method as claimed in claim 1, wherein the output changes dependent upon whether the user is alone or accompanied.

13. A method as claimed in claim 1, wherein the output changes by providing tactile output, or a different graphical user interface enabling a user to control the apparatus via one or more user-selectable items.

14. A method as claimed in claim 1, wherein the output is provided via a mounted head display.

15. An apparatus comprising:
at least one processor; and
at least one memory including computer program code;
wherein the at least one memory and the computer program code are configured to, with the at least one processor, enable the apparatus to:
repeatedly and automatically, obtain a detection of at least one bio-signal of a user of an apparatus;
determine a particular mode of operation of the apparatus in which the apparatus operated when a particular changed bio-signal was detected as changing from a first state to a second state, wherein the apparatus has a plurality of different modes of operation and wherein each different mode of operation is defined by which of at least a first application or a second application is running; and
use a bio-signal profile to determine an output to be provided by comparing each of the first state and the second state of the particular changed bio-signal to a normal range for the particular mode of operation according to the bio-signal profile,
wherein the output is determined dependent upon (1) the particular changed bio-signal having changed (a) from being outside the normal range to inside the normal range, or (b) from being inside the normal range to outside the normal range, and (2) the particular mode of operation of the apparatus in which the apparatus operated when the particular changed bio-signal was detected as changing,
wherein, in an instance in which it is determined that the particular mode of operation is a first mode of operation in which the apparatus runs the first application but not the second application, the output determined changes in response to the particular changed bio-signal changing from the first state to the second state, and
wherein, in an instance in which it is determined that the particular mode of operation is a second mode of operation in which the apparatus runs the second application but not the first application, the output determined does not change in response to the particular changed bio-signal changing from the first state to the second state.

16. The apparatus as claimed in claim 15, wherein the bio-signal profile comprises data collected over at least weeks relating to a plurality of different modes of operation of the apparatus.

17. A physical entity embodying a computer program comprising computer program instructions that, when executed by at least one processor, enable an apparatus at least to perform:

repeatedly and automatically, obtaining a detection of at least one bio-signal of a user of an apparatus;

determining a particular mode of operation of the apparatus in which the apparatus operated when a particular changed bio-signal was detected as changing from a first state to a second state, wherein the apparatus has a plurality of different modes of operation and wherein each different mode of operation is defined by which of at least a first application or a second application is running; and using a bio-signal profile to determine an output to be provided by comparing each of the first state and the second state of the particular changed bio-signal to a normal range for the particular mode of operation according to the bio-signal profile, wherein the output is determined dependent upon (1) the particular changed bio-signal having changed (a) from being outside the normal range to inside the normal range, or (b) from being inside the normal range to outside the normal range, and (2) the particular mode of operation of the apparatus in which the apparatus operated when the particular changed bio-signal was detected as changing, wherein, in an instance in which it is determined that the particular mode of operation is a first mode of operation in which the apparatus runs the first application but not the second application, the output determined changes in response to the particular changed bio-signal changing from the first state to the second state, and wherein, in an instance in which it is determined that the particular mode of operation is a second mode of operation in which the apparatus runs the second application but not the first application, the output determined does not change in response to the particular changed bio-signal changing from the first state to the second state.

* * * * *